United States Patent [19]

Gusakov

[11] Patent Number: 5,184,112
[45] Date of Patent: Feb. 2, 1993

[54] BED PATIENT POSITION MONITOR

[75] Inventor: Ignaty Gusakov, East Aurora, N.Y.

[73] Assignee: Gaymar Industries, Inc., Orchard Park, N.Y.

[21] Appl. No.: 757,621

[22] Filed: Sep. 11, 1991

[51] Int. Cl.⁵ .............................................. G08B 21/00
[52] U.S. Cl. .................................... 340/573; 340/666; 340/691
[58] Field of Search .................. 340/573, 691, 666

[56] References Cited

U.S. PATENT DOCUMENTS

| | | | |
|---|---|---|---|
| 3,439,358 | 4/1969 | Salmons | 340/573 |
| 3,533,095 | 10/1970 | Collins | 340/573 |
| 3,781,843 | 12/1973 | Harrison et al. | 340/573 |
| 3,798,596 | 3/1974 | Sumiyoshi et al. | 340/691 |
| 4,020,482 | 4/1977 | Feldl | 340/573 |
| 4,068,870 | 1/1978 | Whitney | 285/320 |
| 4,175,263 | 11/1979 | Triplett et al. | 340/573 |
| 4,228,426 | 10/1980 | Roberts | 340/573 |
| 4,242,672 | 12/1980 | Gault | 340/573 |
| 4,337,726 | 7/1982 | Czekajewski et al. | 119/1 |
| 4,454,615 | 6/1984 | Whitney | 5/449 |
| 4,483,030 | 11/1984 | Flick et al. | 5/458 |
| 4,520,354 | 5/1985 | Umeda et al. | 340/691 |
| 4,633,237 | 12/1986 | Tucknot et al. | 340/573 |
| 4,638,307 | 1/1987 | Swartout | 340/666 |
| 4,700,180 | 10/1987 | Vance | 340/573 |
| 4,899,133 | 2/1990 | Bartlett | 340/573 |
| 4,907,845 | 3/1990 | Wood | 340/573 |

Primary Examiner—Glen R. Swann, III
Attorney, Agent, or Firm—Young & Thompson

[57] ABSTRACT

An apparatus for monitoring the position of a patient relative to a bed signals whether the patient is in the middle of the bed, to the left or right of center, at the left or right edge of the bed, attempting to lift himself from the bed, or completely out of the bed.

24 Claims, 4 Drawing Sheets

FIG. 4

BED PATIENT POSITION MONITOR

CROSS REFERENCE TO RELATED APPLICATION

Cross reference is hereby made to related U.S. application Ser. No. 07/668,062 filed on Mar. 12, 1991, U.S. Pat. No. 5,140,309 for a SENSOR, and naming Ignaty Gusakov as applicant and Gaymar Industries, Inc. as assignee.

BACKGROUND OF THE INVENTION

1. Field of the Invention

The present invention relates to an apparatus for use in monitoring the position of a patient relative to a support surface such as a bed.

2. Description of the Prior Art

There is a need for effective signalling of a caregiver when a patient moves from one position to another in a bed. For example, such a need exists when a patient, who is likely to suffer injury and sometimes death by leaving his bed without assistance, falls or gets out of bed.

Various patient monitors are known in the prior art. For example, U.S. Pat. No. 4,020,482 to Feldl relates to a patient monitor including an elongated air inflated flexible bag placed below a mattress and connected to a pressure actuated electrical switch at a remote station. The switch is a normally closed low pressure switch which remains open as long as a patient's weight is on the mattress and closes when the patient's weight is removed. In essence, removal of the weight lowers the pressure in the bag which closes the switch.

U.S. Pat. No. 3,533,095 to Collins is of interest in that an air mattress is provided upon which an animal is placed in a first position. For example, a mare is placed upon the mattress in a standing position. When the mare lies down the displacement of her weight causes air from the mattress to expand into a connection to a normally open pressure switch, thereby closing the switch and activating an alarm.

U.S. Pat. No. 3,781,843 to Harrison et al. is of interest in that pressurized fluid is contained in members having a fluid filled passageway which can be attached to the side rails, etc. of a bed. When someone gets out of the bed he typically will grasp such rails and activate an alarm.

U.. Pat. No. 4 175 263 to Triplett et al. is of interest in that it relates to a plurality of pressure sensors for sensing when a patient is in the normal position in a bed and when a patient begins to leave the bed. A pressure sensitive switch and an alarm are also provided.

U.S. Pat. No. 4,633,237 to Tucknott et al. describes a patient bed alarm system which includes multiple sensors which define interstices of a matrix woven into a mat for placement on a bed. The system is used in combination with a microprocessor control. The presence of the patient's body at various combinations of sensors is used to identify the location of the patient and an alarm is provided if the combination of sensors indicate impending vacation of the bed.

U.S. Pat. No. 3,439,358 to Salmons describes detecting movement of a human upon a bed by generating electrical signals which are received by receiving means such as a receiving antenna. Signals are thereby provided for recording such movement.

U.S. Pat. No. 4,907,845 to Wood describes a bed patient monitoring system for determining whether there is a likelihood that the patient is trying to leave the bed. To this end a sensor which utilizes ribbon switches is placed under the mattress next to the bed frame.

U.S. Pat. No. 4,228,426 to Roberts, U.S. Pat. No. 4,242,672 to Gault, U.S. Pat. No. 4,638,307 to Swartout and U.S. Pat. No. 4,700,180 to Vance relate to the use of electrical switches which are directly actuated by contacts which close under the weight of a patient and open when such weight is removed to activate an alarm which indicates the presence or absence of a patient relative to a bed.

United States patents of general interest regarding the monitoring of movement include U.S. Pat. Nos. 4,337,726 and 4,899,133 to Czekajewski et al and Bartlett, respectively.

It is an object of the present invention to provide a position monitor, for use with a patient in a bed, which is relatively simple in construction.

It is another object of the present invention to provide a position monitor for use with a patient in a bed to alert the caregiver when the patient has moved from an original location after placement upon a support surface.

It is also an object of the present invention to provide such a position monitor which will alert the caregiver when the patient has moved off center towards an edge of a support surface.

Another object of the present invention is to provide such a position monitor which will alert the caregiver when the patient has actually moved to an edge of a support surface.

A further object of the present invention is to provide such a position monitor for use with a patient in a bed which will allow the caregiver to determine that a patient is about to fall or get out of the bed before the eventuality occurs.

Yet another object of the present invention is to provide such a position monitor which will alert the caregiver that the patient is in the middle of the bed.

It is also an object of the present invention to provide such a position monitor which will alert the caregiver when a patient is lifting his body away from the middle of a bed in a possible attempt to leave the bed.

SUMMARY OF THE INVENTION

This invention achieves these and other results by providing an apparatus for monitoring the position of a body relative to a support surface. The apparatus includes means for providing an alarm signal and means for activating the alarm signal means in response to movement of a body from a first position to a second position relative to the support surface. The activating means includes at least a first switch and a second switch. Means is provided for connecting the activating means to the alarm signal means for selectively activating the alarm signal means in response to such movement. The connecting means comprises at least a first filter means having an input electrically connected to the first switch, and an output, and a second filter means having an input electrically connected to the second switch, and an output. The connecting means also includes at least a first inverter means having an input electrically connected to the output of the first filter means, and an output, and a second inverter means having an input electrically connected to the output of the second filter means, and an output. The connecting means also includes first, second and third means for sending alarm signals. In particular, a first means is provided having inputs electrically connected to the outputs of the inverter means and an output electrically connected to the alarm signal means for sending a first alarm signal to the alarm signal means. A second means is provided having inputs electrically connected to at least the outputs of the filter means, and an output electrically connected to the alarm signal means, for sending a second alarm signal to the alarm, signal means. A third means is provided having inputs electrically connected to the outputs of the filter means and the inverter means, and a first output electrically connected to the alarm signal means for sending a third alarm signal to the alarm signal means.

In one embodiment, an apparatus is provided for monitoring the position of a patient relative to a support surface comprising means for sensing movement of a patient from a first position to a second position relative to the support surface. Such sensing means includes at least a first sensor and a second sensor. Means is provided for producing an alarm signal including at least a first alarm member, a second alarm member and a third alarm member. In addition, means is provided for connecting the sensing means to the alarm signal means for selectively activating the alarm signal means in response to patient movement. The connecting means includes at least a first and second filter means each having an input electrically connected to first and second sensors, respectively, and at least a first and second inverter means each having an input electrically connected to the output of a first and second filter means, respectively. The connecting means also includes first, second and third means for sending a first alarm signal, second alarm signal and third alarm signal to a first alarm member, second alarm member and third alarm member, respectively. The first means has inputs electrically connected to the outputs of the inverter means and an output electrically connected to the first alarm member. The second means has inputs electrically connected to at least the output of the filter means and an output electrically connected to the second alarm member. The third means has inputs electrically connected to the outputs of the filter means and the inverter means and a first output electrically connected to the third alarm member.

BRIEF DESCRIPTION OF THE DRAWINGS

This invention can be clearly understood by reference to the attached drawings in which.

DESCRIPTION OF THE PREFERRED EMBODIMENT

Figure 1:
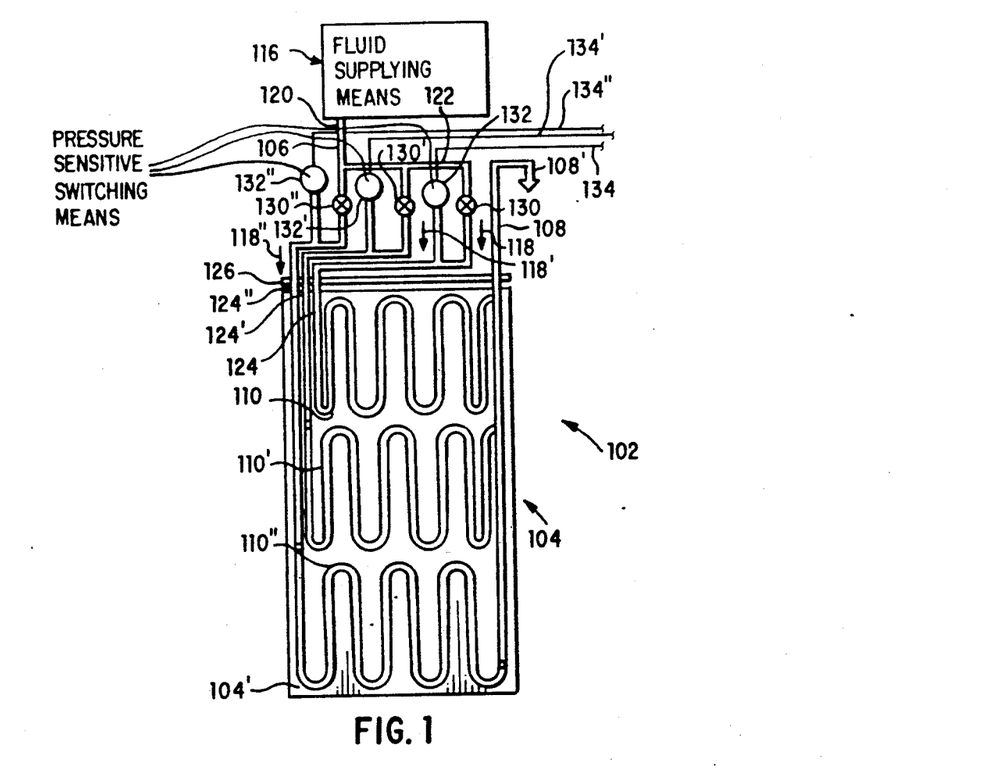
FIG. 1 is a diagrammatic representation of one embodiment of the present invention.
Figure 2:
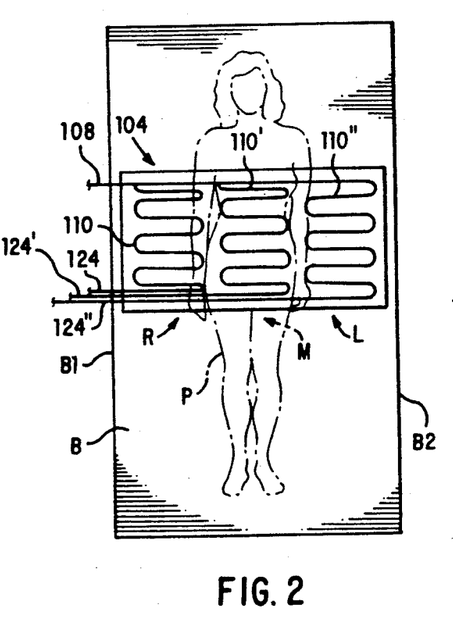
FIG. 2 is a diagrammatic representation of the embodiment of FIG. 1.
Figure 3:
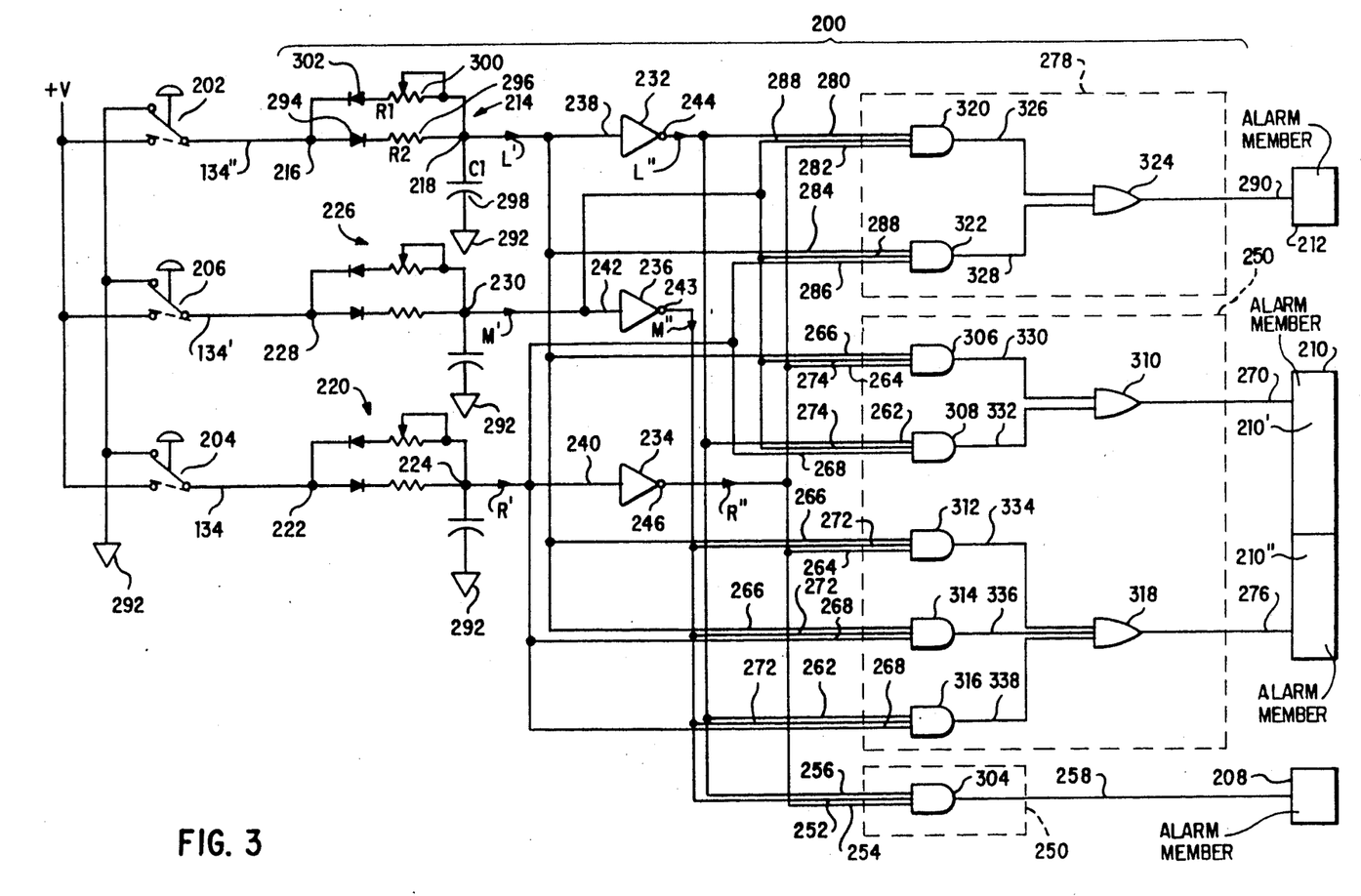
FIG. 3 is a schematic view of the connecting means of FIG. 1.

The embodiment of this invention which is illustrated in FIGS. 1 to 3 is particularly suited for achieving the objects of this invention. FIG. 1 depicts apparatus 102 which includes a resilient means 104 through which fluid under pressure can flow from an inlet 106 for the resilient means 104 through an open outlet 108 for the resilient means 104. The resilient means 104 includes a plurality of tubes, cells or other resilient fluid passages 110, 110', 110" which are collapsed by the weight of a patient as described herein. It is preferred that fluid passages 110' and 110" be non-collapsible where they extend upon the resilient means 104 adjacent to fluid passage 110, and that fluid passage 110" also be non-collapsible where it extends upon the resilient means 104 adjacent fluid passage 110'. In a like manner it is preferred that the outlet 108 be non-collapsible at least where it extends upon the resilient means 104 from its connection to fluid passage 110 to its connection to fluid passage 110".

A fluid supplying means 116 such as a pump is connected at pump outlet 120 to the inlet 106 for continuously supplying fluid under pressure toward the resilient means 104 in the direction of arrows 118, 118', 118". To this end, inlet 106 is connected to a manifold 122. If desired, the fluid supplying means can be the same pump used to inflate an air cushion-type overlay such as is manufactured by Gaymar Industries, Inc. under Model Numbers APP30, APP50, AFP255 and AFP355. Each fluid passage 110, 110', 110" includes a respective fluid passage inlet 124, 124', 124" which is connected to manifold 122. Inlets 124, 124', 124" can be connected directly to manifold 122 or, as depicted in FIG. 1, can be connected to the manifold through a pneumatic connector 126. An example of such a pneumatic connector is described in U.S. Pat. No. 4,068,870 to Whitney and assigned to the assignee of the present invention, Gaymar Industries, Inc. A plurality of pressure sensitive switching means 132, 132', 132" is provided, each switching means monitoring the pressure between orifices 130, 130', 130", respectively, which in turn are connected to the fluid supplying means 116, and a respective fluid passage 110, 110', 110" as depicted in FIG. 1. By way of example only, in the embodiment of FIG. 1, each switching means 132, 132', 132" can include normally open contacts, the contacts in each switching means including outputs 134, 134', 134". Orifices 130, 130', 130" are connected between the fluid supplying means 116 and a respective switching means 132, 132', 132". An example of such an orifice is a flat plate or disc having an aperture therethrough the dimensions of which will depend upon the degree to which it is desired to create back pressure in the fluid passages 110, 110', 110".

In the embodiment of FIGS. 1 and 2, the passages 110, 110', 110" are in the form of tubes attached to or made integral with a thin and flexible plastic base 104 by means of heat sealing, gluing and the like. In a preferred embodiment, the passages 110, 110' 110" are formed by sealing or welding together two or more layers of plastic film. Heat sealing or welding together layers of plastic film is described in U.S. Pat. No. 4,483,030 to Flick et al. which is assigned to Medisearch PR, Inc., a wholly owned subsidiary of the same assignee as this invention, Gaymar Industries, Inc. In the preferred embodiment, the resilient means includes at least two fluid passages. In the embodiment of FIGS. 1 and 2, there are three such passages 110, 110', 110". Each passage 110, 110' 110" includes a serpentine pattern which includes five turns. More or fewer turns can be provided if desired. The fluid passages 110, 110', 110" operate independently as far as the patient load is concerned.

Without limitation, the resilient means 104 is of the type which can be positioned directly beneath or on top of a bed mattress, or if desired between the mattress and a tissue pressure relieving bed pad or cushion such as a foam pad, or an air cushion as is described in U.S. Pat. No. 4,483,030, referred to above, or U.S. Pat. No. 4,454,615 to Whitney which is assigned to Medisearch PR, Inc. to provide signalling means to a caregiver who is monitoring the position of a person relative to a support surface such as a bed.

Figure 2A:
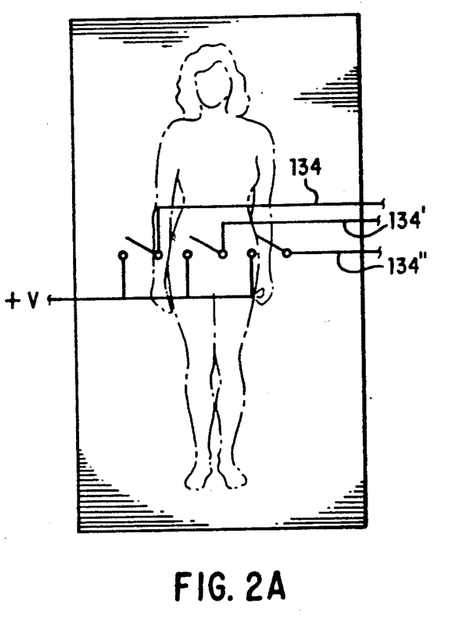
FIG. 2A is a diagrammatic representation of an alternative embodiment of the present invention.

The preferred embodiment thus far described includes means for sensing movement of the body P from a first position to a second position relative to the support surface B. Such sensing means includes fluid passages operating in combination with respective switching means to provide at least a first sensor and a second sensor. In the embodiment of FIGS. 1 to 3, such sensing means includes three sensors 110, 132; 110', 132'; and 110", 132", respectively. The switching means 132 includes a pressure sensitive switch 204, and the switching means 132' includes a pressure sensitive switch 206, and the switching means 132" includes a pressure sensitive switch 202 as seen in FIG. 3. The connecting means described hereinafter is not limited to use with sensors which include fluid passages and pressure switching means as described herein. For example, although the description herein is with reference to pressure switches, other types of switches, transducers and the like can be used with the connecting means of the present invention. The sensors 110, 132; 110', 132'; and 110", 132" can be replaced with electrical switches, if desired. In other words, each combined fluid passage and pressure switch associated therewith which make up each sensor can be replaced by any of many well known types of electrical switches which can be selectively disposed upon the support surface in a manner similar to the disposition of such fluid passages. For example, as depicted in FIG. 2A, the sensors may comprise one or more first electrical switches disposed right (R) of center of the support surface, one or more second electrical switches disposed left (L) center of the support surface, and one or more third electrical switches disposed at the middle (M) of the support surface, each switch being connected to a respective connecting means in the same manner as the corresponding sensors 110, 132; 110', 132'; and 110", 132" are connected to a respective connecting means as described hereinafter. Nor is the present invention limited to the number or the disposition of the sensors as described herein. The present invention is adaptable to other known apparatus which can provide an output signal to the connecting means described hereinafter when a patient has moved from one position to another relative to a support surface. However, the present invention is particularly useful in combination with the pneumatic apparatus described herein.

With particular reference to FIG. 3, the preferred embodiment also includes means for providing an alarm signal which includes at least a first alarm member 208, a second alarm member 210 and a third alarm member 212. Each alarm member 208, 210, 212 can be audible or visual or both and can include, for example, an alarm lamp, an alarm buzzer, or an combination of the two.

The preferred embodiment is of particular interest regarding the means for connecting the sensing means to the alarm signal means for selectively activating the alarm signal means in response to movement of a person P relative to the support surface B. Such connecting means is generally designated 200 in FIG. 3 and includes a first filter means which is depicted by way of example as an R-C filter 214 having an input 216 electrically connected to the switch 202 by output 134", and an output 218, a second filter means which is depicted by way of example as an R-C filter 220 having an input 222 electrically connected to the switch 204 by output 134, and an output 224, and a third filter means which is depicted by way of example as an R-C filter 226 having an input 228 electrically connected to the switch 206 by output 134', and an output 230.

The connecting means also includes a first inverter means which is depicted as an inverter 232, a second inverter means which is depicted as an invertor 234, and a third inventer means which is depicted as an inverter 236. Inverters 232, 234, 236 have inputs 238, 240, 242, respectively, and outputs 244, 246, 248, respectively.

The connecting means also includes first means 250 for sending a first alarm signal to the first alarm member 208. First means 250 has an input 252 electrically connected to the output 248 of the third inverter 236, and input 254 electrically connected to the output 246 of the second inverter 234, an input 256 electrically connected to the output 244 of the first inverter 232, and an output 258 electrically connected to the first alarm member 208. In the preferred embodiment, the first means 250 sends a first alarm signal to the first alarm member 208 when the person P has moved from a position of exerting a force against the support surface B to a position of not exerting a force against support surface B, such as when a patient falls out of or otherwise leaves a bed.

The connecting means also includes second means 260 for sending a second alarm signal to the second alarm member. In the preferred embodiment, the second means 260 sends such second alarm signal to the second alarm member 210 when the person P is off center relative to the support surface B, such as when a patient begins to roll to the right or left of the center of a mattress or other support surface positioned upon a bed frame.

In the preferred embodiment, the second means 260 is also for sending an alternate second alarm signal to the second alarm member 210. In the preferred embodiment, the second means 260 sends such alternate second alarm signal to the second alarm member 210 when the person P moves to one of the edges of the support surface B, such as when a patient has rolled to the right or left edge of a mattress or other support surface positioned upon a bed frame. Second means 260 includes inputs 262, 264, 266 and 268 electrically connected to the outputs of the first inverter 232, second inverter 234, first filter 214 and second filter 220, respectively, and a first output 270 electrically connected to the second alarm member 210. In the preferred embodiment, the second means 260 also includes input 272 and 274 electrically connected to the output of the third inverter 236 and the third filter 226, respectively, and a second output 276 electrically connected to said second alarm member 210.

The connecting means also includes a third means 278 for sending a third alarm signal to the third alarm member 212. Third means 278 includes inputs 280, 282, 284, 286 and 288 electrically connected to the output of first inverter 232, second inverter 234, first filter 214, second filter 220, and third filter 226, respectively, and an output 290 electrically connected to the third alarm member 212. In the preferred embodiment, the third means 278 sends such third alarm signal to the third alarm member 212 when the person P is centered relative to the support surface B, such as when a patient is positioned substantially in the center of a mattress or other support surface positioned upon a bed frame.

Referring to FIG. 3, the outputs 218, 230, 224 of filters 214, 226, 220, respectively, are electrically connected to inputs 238, 242, 240 of inverters 232, 236, 234, respectively. The pressure switch contacts are of the double pole single throw variety with the normally closed pole connected to circuit common or ground 292.

When the apparatus is in an operational mode, a positive dc voltage is connected to normally open poles of the pressure sensitive switches 202, 204, 206 as depicted in FIG. 3. Switches 202, 204, 206 will be activated by the collapsing of fluid passages 110", 110, and 110', respectively, under the weight of a patient P. When in a collapsed condition, such fluid passage will be referred to herein as being loaded. When the weight of the patient has been removed from a fluid passage so that such resilient fluid passage is no longer collapsed, such fluid passage will be referred to herein as being unloaded. When a fluid passage is unloaded, there will be zero or low pressure at a corresponding pressure switch, and such switch will be in the open position depicted in solid lines in Figure 3 and will provide a current path to ground 292 discharging the stored voltage in respective filters 214, 226, 220. When a fluid passage is loaded, pressure will be high at a corresponding pressure switch, and such switch will be in the closed position depicted in broken lines in FIG. 3 and will provide positive voltage to a respective filter 214, 226, 220.

In considering pressure switch 202 and filter 214, when fluid passage 110" is collapsed under the weight of a patient pressure switch 202 senses an increase in pressure that exceeds its trip point and the normally open contact will close as shown by the broken line. Positive voltage will then be connected to diode 294. Current will flow through resistor 296 and charge capacitor 298 which is connected to the circuit common 292. Voltage will increase across capacitor 298 as determined by the time constant R2C1. This voltage will be in the form of signal L' which is connected to the input of inverter 232 and to various AND gate logic circuits as depicted in FIG. 3 and discussed herein. When the weight of the patient is removed from the fluid passage 110" and it is no longer collapsed, pressure in the pressure switch will drop below the trip pressure level, the switch will once again be opened and assume the position shown at switch 202 by the solid line, and the input to the filter 214 will be reduced to zero volts. Capacitor 298 will discharge through variable resistor 300 and diode 302 to circuit common 292 through switch 202. Such discharge will occur at a rate determined by the time constant R1C1 and can be adjusted by the variable resistor or potentiometer 300. In most instances, the time constant R1C1 will be greater than the time constant R2C1 which permits rapid charging of capacitor 298 and slower discharging of capacitor 298. In this manner, a means is provided for reducing or eliminating nuisance tripping of the apparatus when the patient moves in the bed as would be normally expected.

Pressure switches 204, 206 and filters 220, 226 are identical to pressure switch 202 and filter 214 and will not be described herein, the mode of operation of each, in response to the condition of fluid passages 110, 110', respectively, being identical to that of the foregoing mode of operation of switch 202 and filter means 214 in response to the condition of fluid passage 110". Filter 226 will produce voltage output signal M' which is connected to the input of inverter 236 and to various AND gates, and filter 220 will produce voltage output signal R' which is conneredgnal R' which is connected to the input of inverter 234 and to various AND gates, as described herein and depicted in FIG. 3. The nature of signals L' (left), R' (right) and M' (middle) will depend upon the condition of left (L) fluid passage 110", right (R) fluid passage 110, and middle (M) fluid passage 110', respectively. When the weight of a patient closes a switch 202, 204, 206 as described herein and thereby produces a signal L', R', M', respectively, such signal will be referred to herein as being high or on. When the weight of the patient is removed from a respective fluid passage so that a switch 202, 204, 206 is opened such that the input to a filter 214, 220, 226, respectively, is zero, as described herein, the signal L', R', M' will be referred to herein as being low or off.

The inverters referred to herein, including inverters 232, 234, 236 are provided with a positive dc voltage (not shown) in a known manner and invert signals L', R' and M', respectively, to provide signals L", R" and M", respectively. In particular, high signals L', R' AND M' will be inverted to low signals L", R", M", and low signals L', R', M' will be inverted to high signals L", R", M".

In the preferred embodiment, first means 250 includes AND gate 304 electrically connected as depicted in FIG. 3. Second means 260 includes AND gates 306 and 308 and OR gate 310, and AND gates 312, 314, and 316, and OR gate 318 electrically connected as depicted in FIG. 3. Third means 278 includes AND gates 320 and 322 and OR gate 324 electrically connected as depicted in FIG. 3. It should be noted that the various AND and OR gates described herein are provided with a positive dc voltage (not shown) in a known manner.

In considering the operation of the apparatus depicted in FIGS. 1 to 3, the left (L) sensing means includes pressure switch 202 and fluid passage 110", the right (R) sensing means includes pressure switch 204 and fluid passage 110, and the middle (M) sensing means includes pressure switch 206 and fluid passage 110'. Depending upon the width of the patient, centering the patient relative to support surface B will cause fluid passage 110' to be loaded or fluid passages 110, 110', 110" to be loaded. In the case of a narrow patient, the middle fluid passage 110' will be loaded thereby closing switch 206 and producing a signal M' which will be high. Since switches 202 and 204 will remain open, signals L' and R' will be low. High signal M' will be sent to AND gate 320 at input 288. Low signals L' and R' will be inverted at inverters 232 and 234, respectively, to produce high signals L" and R", respectively, which will be sent to AND gate 320 at inputs 280 and 282, respectively. OR gate 324 will accept a high signal from AND gate 320 at input 326 and send a high signal at output 290 to activate alarm member 212 signifying the patient is in the middle of the support surface.

Similarly, if the patient is wide, all three fluid passages 110, 110', 110" will be loaded thereby closing switches 204, 206, 202, respectively, and producing high signals R', M', L' which be sent to AND gate 322 at inputs 286, 288, 284, respectively. OR gate 324 will accept a high signal from AND gate 322 at input 328 and send a high signal at output 290 to activate alarm member 212 signifying that the patient is in the middle of the support surface.

If the patient is completely out of the bed, all of the switches 202, 206, 204 will be open and signals L', M', R' will be low. Inverters 232, 236, 234 will invert such signals to provide high signals L", M", R" which will be sent to AND gate 304 at inputs 256, 252, 254, respectively. AND gate 304 will send a high signal at output 258 to activate alarm member 208 signifying that the patient is not on the support surface.

If the patient moves off center towards the left of support surface B fluid passages 110', 110" will be loaded thereby closing switches 206, 202 and producing high signals M', L'. Fluid passage 110 will be unloaded and switch 204 will remain open so that R' will be low. High signals M', L' will be sent to AND gate 306 at inputs 274 and 266, respectively. Low signal R' will be inverted at inverter 234 to produce high signal R" which will be sent to AND qate 306 at input 264. OR gate 310 will accept a high signal from AND gate 306 at input 330 and send a high signal at output 270 to actuate an alarm member 210' of second alarm member 210 signifying that the patient has moved slightly off center.

If the patient moves off center towards the right of support surface B fluid passages 110', 110 will be loaded thereby closing switches 206, 204 and producing high signals M', R'. Fluid passage 110" will be unloaded and switch 202 will remain open so that L' will be low. High signals M', R' will be sent to AND gate 308 at inputs 274 and 268, respectively. Low signal L' will be inverted at inverter 232 to produce high signal L" which will be sent to AND gate 308 at input 262. OR gate 310 will accept a high signal from AND gate 308 at input 332 and send a high signal at output 270 to actuate alarm member 210' signifying that the patient has moved slightly off center.

If the patient moves to the left edge B2 of support surface B only fluid passage 110" will be loaded thereby closing switch 202 and producing a high signal L'. Fluid passages 110, 110' will be unloaded and switches 204, 206 will remain open so that R', M' will be low. High signals L' will be sent to AND gate 312 at input 266. Low signal R', M' will be inverted at inverters 234, 236 to produce high signals R", M" which will be sent to AND gate 312 at inputs 264, 272. OR gate 318 will accept a high signal from AND embpt a high signal from AND gate 312 at input 334 and send a high signal at output 276 to actuate an alarm member 210" of second alarm member 210 signifying that the patient has moved to the left edge of the support surface.

If in an effort to get out of bed the patient lifts his body from the bed by making a movement similar to a push-up such that the arms push down upon the right and left side of the bed to lift the body upwards away from the middle of the bed, fluid passages 110, 110" will be loaded thereby closing switches 204, 202 and producing high signals R', L'. Fluid passage 110' will be unloaded and switch 206 will remain open so that M' will be low. High signals R', L' will be sent to AND gate 314 at inputs 268 and 266, respectively. Low signal M' will be inverted at inverter 236 to produce high signal M" which will be sent to AND gate 314 at input 272. OR gate 318 will accept a high signal from AND gate 314 at input 272. OR gate 318 will accept a high signal from AND gate 314 at input 336 and send a high signal at output 276 to actuate alarm member 210" signifying that the patient might be making an effort to get out of bed.

If the patient moves off center to the right edge B1 of support surface B fluid passage 110 will be loaded thereby closing switch 204 and producing high signals R'. Fluid passages 110', 110" will be unloaded and switch 206, 202 will remain open so that M', L' will be low. High signal R' will be sent to AND gate 316 at input 268. Low signals M', L' will be inverted at inverter 236, 232 to produce high signal M", L" which will be sent to AND gate 316 at input 272, 262. OR gate 318 will accept a high signal from AND gate 316 at input 338 and send a high signal at output 276 to actuate second alarm member 210" signifying that the patient has moved to the right edge of the support surface.

Figure 4:
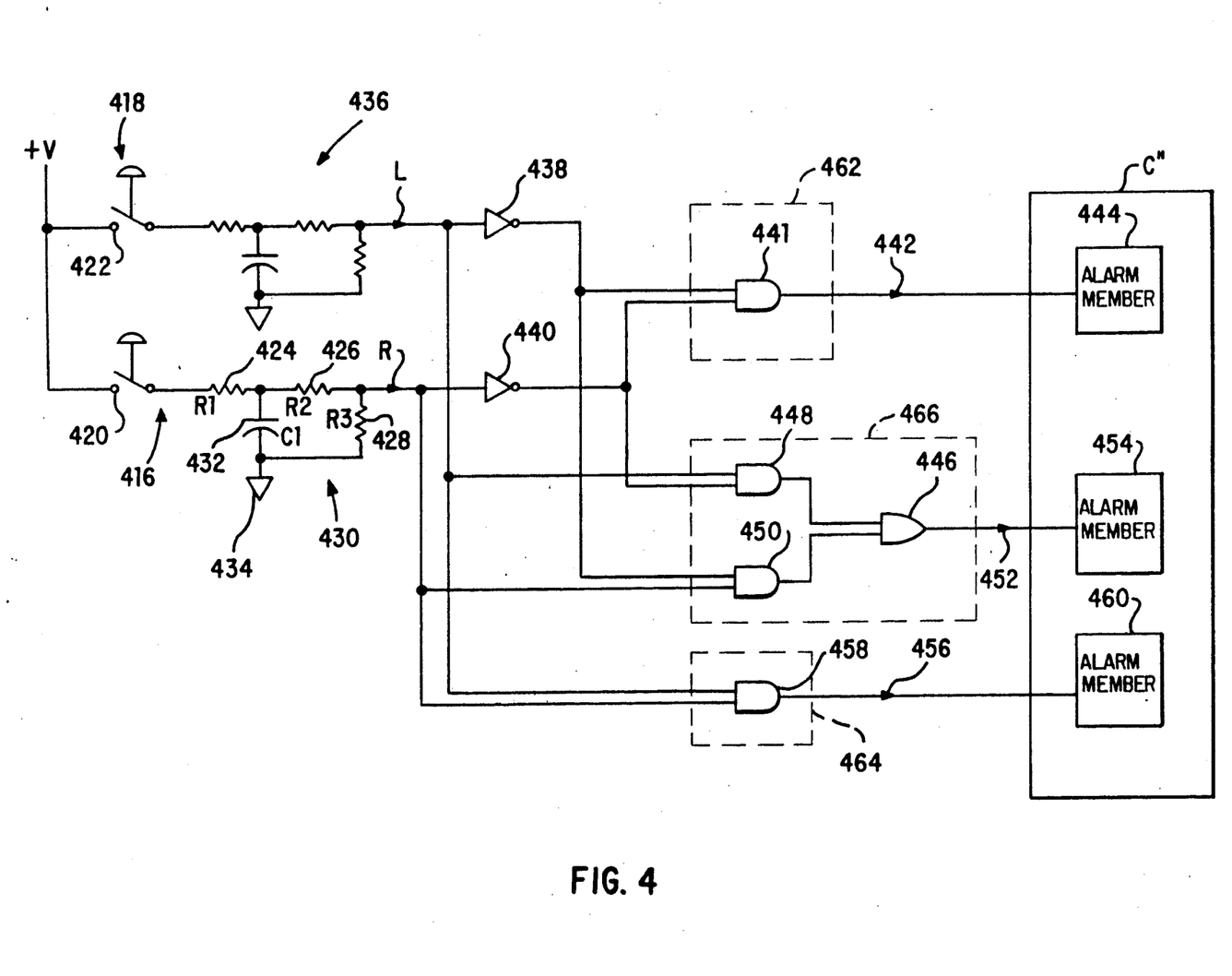
FIG. 4 is a schematic view of an alternative connecting means.
Figure 5:
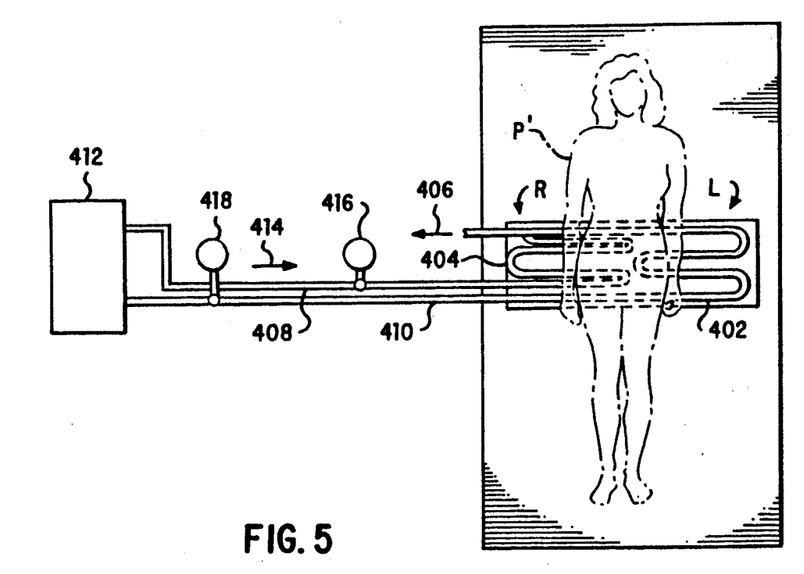
FIG. 5 is a diagrammatic representation of an embodiment which includes the connecting means of FIG. 4.

FIGS. 4 and 5 depict a simplified version of the present invention and include an apparatus including two sensing means placed side by side as depicted in FIG. 5. As in the embodiment of FIG. 2, the patient P' is depicted lying on a support surface B' such as a mattress. Each sensing means includes a fluid passage 402 and a fluid passage 404. The common outlet 406 of the fluid passages is vented to atmosphere. The inlets 408, 410 are connected to an air pump 412 which supplies a fluid such as air under pressure in the direction of arrow 414. Pressure switch 416 senses an increase in pressure when right (R) fluid passage 404 is loaded. Pressure switch 418 senses an increase in pressure when left (L) fluid passage 402 is loaded.

Referring to the schematic of FIG. 4, a positive dc voltage +V is connected to the normally open contacts 420, 422 of pressure switches 416, 418, respectively. When pressure switch 416 senses an increase in pressure, contact 420 will be closed and connect voltage +V to resistor 424. Resistors 424, 42 divider and the resistance portion of the R-C filter 430. Capacitor 432 forms the remainder of the R C filter 430. The R-C filter allows for rapid charging of capacitor 432 through resistor 424 when the normally open single pole single throw contact 420 closes as a result of the weight of the patient causing fluid passage 404 to collapse or be loaded. When the weight of the patient is removed from fluid passage 404 it resumes its usual noncollapsed or unloaded state causing a reduction of pressure at pressure switch 416 and an opening of contact 420. This causes capacitor 432 to discharge through resistors 426 and 428 to circuit common or ground 434. The discharge time constant is determined by the product of C1 and R2 plus R3. The steady state voltage across C1 is determined by the product of +V and the ratio (R2+R3)/(R1+R2+R3). The voltage signal represents a right (R) output signal after filtering to prevent nuisance tripping during normal patient movements. The amount of filtering is determined by the values of C1 and the values of R1, R2 and R3. These resistors can be made adjustable.

R-C filter 436 is identical to R-C filter 430. When pressure switch 418 senses an increase in pressure, contact 422 will be closed and connect voltage +V to the R-C filter 436, in the same manner as discussed above regarding R-C filter 430, to produce a voltage signal representing a left (L) output signal after filtering.

Signals L and R are inverted by inverters 438 and 440, respectively.

Considering the schematic of FIG. 4, the output 442 of AND gate 441 will go high to activate alarm member 444 when both the left signal L and the right signal R are low indicating corresponding low pressure resulting from the patient being off of both fluid passages 402, 404. Similarly, the output of OR gate 446 will go high when the patient is off of either the left fluid passage 402 or the right fluid passage 404. In particular, the inputs to OR gate 446 are from AND gates 448 a6 a46 are from AND gates 448 and 450. The output of AND gate 448 will go high when the left fluid passage 402 is compressed and the right fluid passage 404 is open as when the patient has moved towards the left. The output of AND gate 450 will go high when the right fluid passage 404 is compressed and the left fluid passage 402 is open as when the patient has moved towards the right. A high input to OR gate 446 from either AND gate 448 or AND gate 450 will result in a high output 452 to activate alarm member 454. Finally, the output 456 of AND gate 458 will go high to activate alarm member 460 when both the left fluid passage 402 and the right fluid passage 404 are compressed as when the patient is in the middle of the support surface B. In the embodiment of FIG. 4, first, second and third means for sending alarm signals to respective alarm members 444, 460 and 454 are depicted in broken lines at 462, 464 and 466, respectively.

Figure 6:
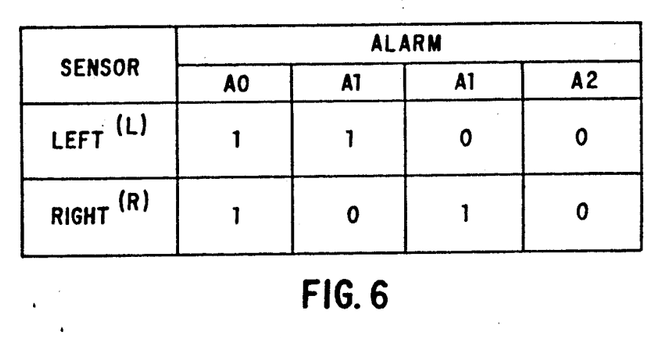
FIG. 6 is a Truth Table of the embodiment of FIGS. 4 and 5.

The operation of the embodiment of FIGS. 4 and 5 can readily be understood with reference to the truth table of FIG. 6. In this table the fluid passages 402, 404 are identified as "Left" and "Right", respectively, the high L, R signals as "1" and the low L,R signals as "0". There are three types of alarms chosen for annunciation although the system need not be limited to three. Alarm A0 signifies that the patient is laying on both the left and right sensors which in turn means that the patient is in the middle of the bed. The left (L) and right (R) signals are high (1). In this mode a green lamp at alarm member 460 might be lit indicating that the patient is in a satisfactory position. Alarm A1 signifies that the patient is on one fluid passage and off the other; that is, that the patient has moved toward one edge of the bed. One of the left (L) or right (R) signals will be high (1) and one will be low (0). In this mode an amber lamp at alarm member 454 might be lit signalling caution and thanter. An audible tone could also be sounded such as an intermittent beep. Alarm A2 signifies that the patient is off both sensors and probably out of bed. The left (L) and right (R) signals are low (0). In this mode a red lamp at alarm 444 might be lit and a steady audible tone might be initiated signalling that there is a problem. The condition where the pressure switch detects pressure caused by the patient laying on a fluid passage is signified by 1. The condition where the patient is off of the fluid passage so that no or low pressure is sensed by the pressure switch is signified by 0. The associated patient conditions described are signified by 1 and 0 symbols in the truth table. These logic conditions are established by the circuit shown in FIG. 4.

Figure 7:
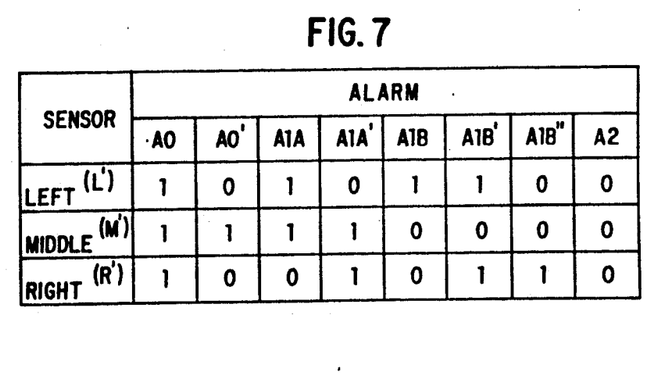
FIG. 7 is a Truth Table of the embodiment of FIGS. 1 to 3.

A similar truth table is depicted in FIG. 7 for the embodiment of FIGS. 1 to 3. In this table, A0, A0' signifies that the patient is in the middle of the bed. For a wider patient who compresses all of the fluid passages 110, 110', 110" all of the signals R', M', L' will be high (1) as designated at A0 causing alarm member 212 to be activated. For a narrower patient who compresses only fluid passage 110', signal M' will be high (1) and signals R', L' will be low (0) as designated by A0' causing alarm member 212 to be activated. A2 signifies that the patient is out of the bed, the signals L', M', R' all being low (0). This will cause alarm member 208 to be activated. A1A, A1A' signifies that the patient has moved off center to the left or right, respectively. In mode A1A, signals L', M' will be high (1) and signal R' will be low (0). In mode A1A', signals R', M' will be high and signal L' will be low. In either condition, alarm member 210' will be activated. A1B, A1B" signifies that the patient has moved to the left edge or right edge of the bed, respectively. In mode A1B, signal L' will be high (1) and signals M', R' will be low (0). In mode A1B'", signal R' will be high (1) and signals L', M' be activated. A1B' signifies that the patient has lifted his body from the middle of the bed and is supporting it by bearing down upon the left and right side of the bed as might occur as the patient begins to make a move to get out of the bed or sit up. In such mode signals L', R' will be high (1) and signal M' will be low (0) which will also activate alarm member 210".

The embodiments which have been described herein are but some of several which utilize this invention and are set forth here by way of illustration but not of limitation. It is apparent that many other embodiments which will be readily apparent to those skilled in the art may be made without departing materially from the spirit and scope of this invention.

I claim:

1. Apparatus for monitoring the position of a body relative to a support surface, comprising:

means for sensing movement of a body from a first position to a second position relative to a support surface, said sensing means including at least a first sensor and a second sensor;

means for providing an alarm signal including at least a first alarm member, a second alarm member and a third alarm member; and means for electrically connecting said sensing means to said alarm signal means for selectively activating saidarm signal means in response to said movement, said connecting means comprising:

at least a first filter means having an input electrically connected to said first sensor, and an output, and a second filter means having an input electrically connected to said second sensor, and an output;

at least a first inverter means having an input electrically connected to said output of said first filter means, and an output, and a second inverter means having an input electrically connected to said output of said second filter means, and an output;

first means, having inputs electrically connected to the outputs of said first and second inverter means and an output electrically connected to said first alarm member for sending a first alarm signal to said first alarm member;

second means having inputs electrically connected to at least the outputs of said first and second filter means, and an output electrically connected to said second alarm member, for sending a second alarm signal to said second alarm member; and third means having inputs electrically connected to the outputs of said first and second filter means and said first and second inverter means, and an output electrically connected to said third alarm member for sending a third alarm signal to said third alarm member.

2. The apparatus of claim 1 wherein said first means is for sending a first alarm signal to said first alarm member when said body has moved from a position of exerting a force against said support surface to a position of not exerting a force against said support surface; wherein said second means is for sending a second alarm signal to said second alarm member when said body is centered relative to said support surface; and wherein said third means is for sending a third alarm signal to said third alarm member when said body is off center relative to said support surface.

3. The apparatus of claim 1 wherein said sensing means further includes a third sensor, said connecting means further comprises a third filter means having an input electrically connected to said third sensor, and an output, and a third inverter means having an input electrically connected to said output of said third filter means, and an output; and wherein said third means has inputs electrically connected to said third filter means and further includes a second output electrically connected to said third alarm member for sending an alternate third alarm signal to said third alarm member.

4. The apparatus of claim 3 wherein said first means is for sending a first alarm signal to said first alarm member when said body has moved from a position of exerting a force against said support surface to a position of not exerting a force against said support surface; wherein said second means is for sending a second alarm signal to said second alarm member when said body is centered relative to said support surface; and wherein said third means is for sending a third alarm signal to said third alarm member when said body is off center relative to said support surface or when said body is near an edge of said support surface.

5. The apparatus of claim 4 wherein each filter means is an R-C filter.

6. The apparatus of claim 5 wherein each sensor includes a pressure switch.

7. The apparatus of claim 6 wherein each sensor further includes a tubular fluid passage connected to a respective pressure switch.

8. The apparatus of claim 3 wherein said third sensor comprises at least one third electrical switch electrically connected to said third filter means.

9. The apparatus of claim 1 wherein each filter means is an R-C filter.

10. The apparatus of claim 1 wherein each sensor includes a pressure switch.

11. The apparatus of claim 10 wherein each sensor further includes a tubular fluid passage connected to a respective pressure switch.

12. The apparatus of claim 1 wherein said first sensor comprises at least one first electrical switch electrically connected to said first filter means and wherein said second sensor comprises at least one second electrical switch electrically connected to said second filter means.

13. An apparatus for monitoring the position of a body relative to a support surface, said apparatus having means for providing an alarm signal including at least a first alarm member, a second alarm member and a third alarm member, and means for sensing movement of a body from a first position to a second position relative to said support surface, said sensing means including (a) at least a first resilient means and a second resilient means through each of which fluid under pressure can flow from an inlet to an outlet, of each resilient means, (b) fluid supplying means connected to each inlet for continuously supplying fluid under pressure to each resilient means, and (c) at least a first switching means and a second switching means connected to said first resilient means and said second resilient means, respectively, for controlling said alarm signal means in response to changes in said pressure, wherein the improvement comprises means for connecting said sensing means to said alarm signal means for selectively activating said alarm signal means in response to said movement, said connecting means comprising:

at least a first filter means having an input electrically connected to said first switching means, and an output, and a second filter means having an input electrically connected to said second switching means, and an output;

at least a first inverter means having an input electrically connected to said output of said first filter means, and an output, and a second inverter means having an input electrically connected to said output of said second filter means, and an output;

first means, having inputs electrically connected to the outputs of said first and second inverter means and an output electrically connected to said first alarm member for sending a first alarm signal to said first alarm member;

second means having inputs electrically connected to at least the outputs of said first and second filter means, and an output electrically connected to said second alarm member, for sending a second alarm signal to said second alarm member; and third means having inputs electrically connected to the outputs of said first and second filter means and said first and second inverter means, and acted to said third alarm member for sending a third alarm signal to said third alarm member.

14. The apparatus of claim 13 wherein said first means is for sending a first alarm signal to said first alarm member when said body has moved from a position of exerting a force against said support surface to a position of exerting a force against said support surface; wherein said second means is for sending a second alarm signal to said second alarm member when said body is centered relative to said support surface; and wherein said third means is for sending a third alarm signal to said third alarm member when said body is off center relative to said support surface.

15. The apparatus of claim 13 wherein said sensing means further includes (a) a third resilient means through which fluid under pressure can flow form an inlet to an outlet of said third resilient means, said fluid supplying means being connected to said inlet of said third resilient means for continuously supplying fluid under pressure to said third resilient means, and (b) a third switching means connected to said third resilient means for controlling said alarm signal means in response to changes in said pressure, and further wherein said connecting means includes a third filter means having an input electrically connected to said third switching means, and an output, and a third inverter means having an input electrically connected to said output of said third filter means, and an output, and wherein said third means has inputs electrically connected to said third filter means and further includes a second output electrically connected to said third alarm member for sending an alternate third alarm signal to said third alarm member.

16. The apparatus of claim 15 wherein said first means is for sending a first alarm signal to said first alarm membe when said body has moved from a position of exerting a force against said support surface to a position of not exerting a force against said support surface; wherein said second means is for sending a second alarm signal to said second alarm member when said body is centered relative to said support surface; and wherein said third alarm memeber when said body is off center relative to said support surface or when said body is near an edge of said support surface.

17. The apparatus of claim 16 wherein each filter means is an R-C filter.

18. The apparatus of claim 17 wherein each sensing means includes a pressure switch.

19. The apparatus of claim 13 wherein each filter means is an R-C filter.

20. The apparatus of claim 13 wherein each sensing means includes a pressure switch.

21. An apparatus for monitoring the position of a patient relative to a support surface, said apparatus having means for providing an alarm signal including at least a first alarm member, a second alarm member, a third movement of a patient from a first position to a second position relative to said support surface, said sensing means including (a) at least a first resilient means, a second resilient means, and a third resilient means through each of which fluid under pressure can flow from an inlet to an outlet, of each resilient means, (b) fluid supplying means connected to each inlet for continuously supplying fluid under pressure to each resilient means, and (c) at least a first pressure sensitive switching means, a second pressure sensitive switching means, and a third pressure sensitive switching means connected to said first resilient means, said second resilient means, and said third resilient means, respectively, for controlling said alarm signal means in response to changes in said pressure, wherein the improvement comprises means for connecting said sensing means to said alarm signal means for selectively activating said alarm signal means in response to said movement, said connecting means comprising:
- at least a first filter means having an input electrically connected to said first switchnnected to said first switching means, and an output, a second filter means having an input electrically connected to said second switching means, and an output, and a third filter means having an input electrically connected to said third switching means, and an output;
- at least a first inverter means having an input electrically connected to said output of said first filter means, and an output, a second inverter means having an input electrically connected to said output of said second filter means, and an output, and a third inverter means having an input electrically connected to said output of said third filter means, and an output;
- first means, having inputs electrically connected to the outputs of said inverter means, and an output electrically connected to said first alarm member for sending a first alarm signal to said first alarm member when said patient has moved from a position of exerting a force against said support surface to a position of not exerting a force against said support surface;
- second means having inputs electrically connected to at least the outputs of said filter means, and an output electrically connected to said second alarm member, for sending a second alarm signal to said second alarm member when said patient is centered relative to said support surface; and
- third means having inputs electrically connected to the outputs of said filter means and said inverter means, a first output electrically connected to said third alarm member for sending a third alarm signal to said third alarm member when said patient is off center relative to said support surface, and a second output electrically connected to said fourth alarm member for sending a fourth alarm signal to said fourth alarm member when said body is near an edge of said support surface or when said patient has exerted a force against said support surface at the left and right of center of said support surface to raise said body off of said center of said support surface.

22. The apparatus of claim 21 wherein each filter means is an R-C filter.

23. An apparatus for monitoring the position of a body relative to a support surface, said apparatus having means for providing an alarm signal, and means for activating said alarm signal means in response to movement of a body from a first position to a second position relative to said support surface, said activating means including at least an switch and a second switch, wherein the improvement comprises means for connecting said activating means to said alarm signal means for selectively activating said alarm signal means in response to said movement, said connecting means comprising:
- at least a first filter means having an input electrically connected to said first switch, and an output, and a second filter means having an input electrically connected to said second switch, and an output;
- at least a first inverter means having an input electrically connected to said output of said first filter means, and an output, and a second inverter means having an input electrically connected to said output of said second filter means, and an output;
- first means, having inputs electrically connected to the outputs of said inverter means and an output electrically connected to said alarm signal means for sending a first alarm signal to said alarm signal means;
- second means having inputs electrically connected to at least the outputs of said filter means, and an output electrically connected to said alarm signal means, for sending a second alarm signal to said alarm signal means; and
- third means having inputs electrically connected to the outputs of said filter means and said inverter means, and a first output electrically connected to said alarm signal means for sending a third alarm signal to said alarm signal means.

24. The apparatus of claim 23 wherein said sensing means further includes a third switch, and further having an input electrically connected to said third switch, and an output, and a third inverter means having an input electrically connected to said output of said third filter means, and an output electrically connected to inputs of said first means and said second means; and wherein said third means further includes a second output electrically connected to said alarm signal means for sending an alternate third alarm signal to said alarm signal means.

* * * * *